US010528793B2

(12) United States Patent
Codella et al.

(10) Patent No.: US 10,528,793 B2
(45) Date of Patent: Jan. 7, 2020

(54) AUTOMATIC IDENTIFICATION OF FOOD SUBSTANCE

(71) Applicant: International Business Machines Corporation, Armonk, NY (US)

(72) Inventors: Noel C. Codella, White Plains, NY (US); Jonathan H. Connell, II, Cortlandt-Manor, NY (US); Hariklia Deligianni, Alpine, NJ (US); Nalini K. Ratha, Yorktown Heights, NY (US); Vince Siu, Thornhill (CA); Hui Wu, White Plains, NC (US)

(73) Assignee: International Business Machines Corporation, Armonk, NY (US)

( * ) Notice: Subject to any disclaimer, the term of this patent is extended or adjusted under 35 U.S.C. 154(b) by 102 days.

(21) Appl. No.: 15/852,082

(22) Filed: Dec. 22, 2017

(65) Prior Publication Data
US 2019/0197289 A1    Jun. 27, 2019

(51) Int. Cl.
*G06K 9/00*     (2006.01)
*G06F 17/30*    (2006.01)
*G01N 33/02*    (2006.01)
*G06F 16/435*   (2019.01)
*G06F 16/583*   (2019.01)
*G06F 16/9038*  (2019.01)

(52) U.S. Cl.
CPC .......... *G06K 9/0014* (2013.01); *G01N 33/02* (2013.01); *G06F 16/437* (2019.01); *G06F 16/583* (2019.01); *G06F 16/9038* (2019.01)

(58) Field of Classification Search
CPC . G06K 9/0014; G06F 16/583; G06F 16/9038; G06F 16/437; G01N 33/02
See application file for complete search history.

(56) References Cited

U.S. PATENT DOCUMENTS

| 9,377,396 B2 | 6/2016 | Goldring | |
| 2014/0147829 A1* | 5/2014 | Jerauld | G06F 1/163 434/430 |
| 2014/0320858 A1 | 10/2014 | Goldring | |
| 2015/0036138 A1 | 2/2015 | Watson | |
| 2016/0091419 A1 | 3/2016 | Watson | |
| 2016/0260352 A1 | 9/2016 | Ortiz | |
| 2016/0290863 A1 | 10/2016 | Goldring | |
| 2016/0307128 A1* | 10/2016 | Herman | G06Q 10/0633 |
| 2017/0003285 A1 | 1/2017 | Sundvor | |
| 2017/0069225 A1 | 3/2017 | Ortiz | |
| 2017/0097342 A1 | 4/2017 | Sundvor | |

(Continued)

*Primary Examiner* — David F Dunphy
(74) *Attorney, Agent, or Firm* — Kristofer Haggerty; Otterstedt, Wallace & Kammer, LLP

(57) ABSTRACT

A method of displaying information relating to an allergen present in a food substance together with a user profile, the method including capturing an image of a scene, segmenting the image to determining at least a segmentation of the food substance in the image, determining a classification of the food substance using the segmentation, determining a presence of the allergen in the food substance using the classification of the food substance and a database of allergens and food substances, determining a risk to a user using the user profile specifying a user sensitivity to the allergen, and displaying an output including a view of the user profile and the image, wherein the image is augmented to identify the presence of the allergen.

20 Claims, 4 Drawing Sheets

(56) References Cited

U.S. PATENT DOCUMENTS

2017/0249445 A1\* 8/2017 Devries .................. G16H 10/60
2017/0254701 A1 9/2017 Goldring et al.
2017/0323174 A1 11/2017 Joshi \* cited by examiner

AUTOMATIC IDENTIFICATION OF FOOD SUBSTANCE

BACKGROUND

The present disclosure relates generally to the identification of a food substance.

There are many conditions under which an individual's body may have an undesirable reaction to certain foods, food groups, ingredients, additives, etc. (referred to herein as food substances). Common examples of food substances that can interfere with normal body functions include milk, eggs, certain fish (e.g., bass, flounder, cod), shellfish (e.g., crab, lobster, shrimp), tree nuts (e.g., almonds, walnuts, pecans), peanuts, wheat, and soybeans. Further, ingredients such as sugar can affect patients with diabetes.

To avoid undesirable reactions, the individual typically takes precautions to avoid ingesting or being exposed to these food substances. Avoiding these food substances can be challenging, particularly when these items are found under different trades names, are components of other ingredients, or where the foods are present as contaminants.

BRIEF SUMMARY

According to an embodiment of the present invention, a method of displaying information relating to an allergen present in a food substance together with a user profile, the method including capturing an image of a scene, segmenting the image to determining at least a segmentation of the food substance in the image, determining a classification of the food substance using the segmentation, determining a presence of the allergen in the food substance using the classification of the food substance and a database of allergens and food substances, determining a risk to a user using the user profile specifying a user sensitivity to the allergen, and displaying an output including a view of the user profile and the image, wherein the image is augmented to identify the presence of the allergen.

As used herein, "facilitating" an action includes performing the action, making the action easier, helping to carry the action out, or causing the action to be performed. Thus, by way of example and not limitation, instructions executing on one processor might facilitate an action carried out by instructions executing on a remote processor, by sending appropriate data or commands to cause or aid the action to be performed. For the avoidance of doubt, where an actor facilitates an action by other than performing the action, the action is nevertheless performed by some entity or combination of entities.

One or more embodiments of the invention or elements thereof can be implemented in the form of a computer program product including a computer readable storage medium with computer usable program code for performing the method steps indicated. Furthermore, one or more embodiments of the invention or elements thereof can be implemented in the form of a system (or apparatus) including a memory, and at least one processor that is coupled to the memory and operative to perform exemplary method steps. Yet further, in another aspect, one or more embodiments of the invention or elements thereof can be implemented in the form of means for carrying out one or more of the method steps described herein; the means can include (i) hardware module(s), (ii) software module(s) stored in a computer readable storage medium (or multiple such media) and implemented on a hardware processor, or (iii) a combination of (i) and (ii); any of (i)-(iii) implement the specific techniques set forth herein.

Techniques of the present invention can provide substantial beneficial technical effects. For example, one or more embodiments may provide one or more of the following advantages:
 high accuracy and sensitivity identification of food or chemical substances;
 low (user) effort identification of food or chemical substances;
 mobile consumer capability of detecting food or chemical substances; and
 unified graphical user interface.

These and other features and advantages of the present invention will become apparent from the following detailed description of illustrative embodiments thereof, which is to be read in connection with the accompanying drawings.

BRIEF DESCRIPTION OF THE SEVERAL VIEWS OF THE DRAWINGS

Preferred embodiments of the present invention will be described below in more detail, with reference to the accompanying drawings.

DETAILED DESCRIPTION

Embodiments of the present invention relate to a method, a system and a user interface facilitating the identification of certain food substances.

According to one or more embodiments of the present invention, a method 100 of detecting food substances includes a joint image segmentation and classification 101 of an image captured by a user's device. For example, an application running on a user's device uses a connected camera to capture an image of a plate of food. The application segments the image to separate objects in the image from one another. The application performs a classification of each object, e.g., identifying a protein, a starch and vegetable foods. The image classification can be performed using existing methods using, for example, an appearance based model of known foods or classification by a neural network image classifier. It should be understood that the classification can use other methods, and that the present invention is not limited to any particular classification method described herein.

According to one or more embodiments of the present invention, the application cross-references each of the segmented and classified food substances with an allergen risk database 102. By cross-referencing the identified food substances with the allergen risk database, the application predicts a risk level for the user. The prediction can be made using, for example, uses a machine learning model According to one or more embodiments of the present invention, the allergen risk database includes a listing of typical raw ingredients and main materials used to make common food dishes. The application includes functionality for a user to input additional dishes and recipes into the allergen risk database. The application extracts the raw ingredients commonly used to prepare a food substance, and determines if the food substance is likely to contain allergens for a given user profile. The method further includes generating a food allergen risk profile for each of the segmented and classified food substances 103 (see also FIG. 4).

According to one or more embodiments of the present invention, visual segmentation and classification is used to understand food content and predict a probability of particular food substance in each localized area of plate. This is a high sensitivity step, identifying regions with any significant risk (e.g., >1%).

Figure 1:
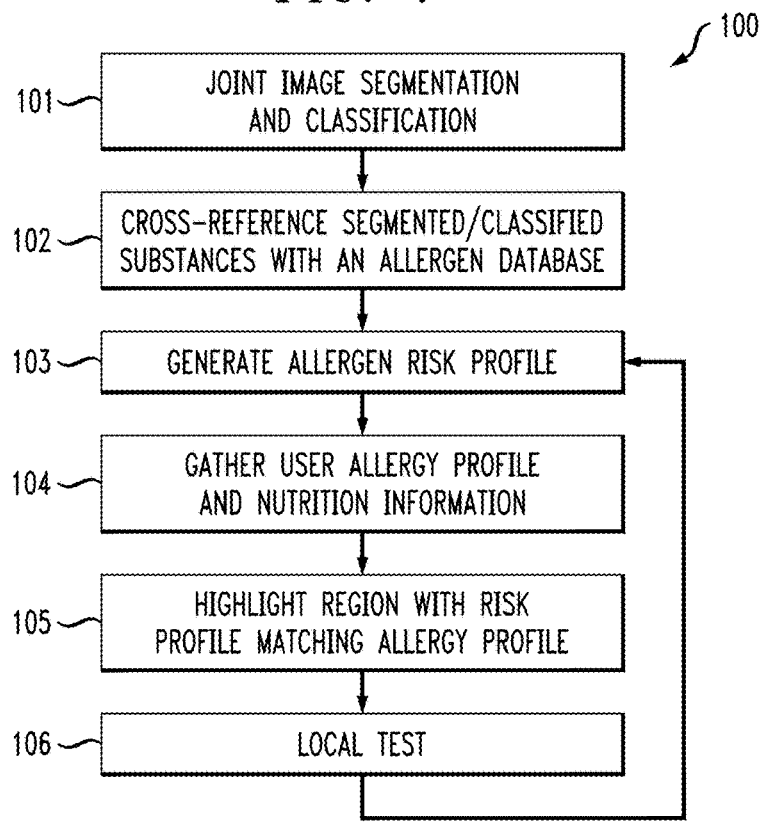
FIG. 1 is flow diagram of a method of identifying potential allergens according to an embodiment of the present invention.
Figure 2:
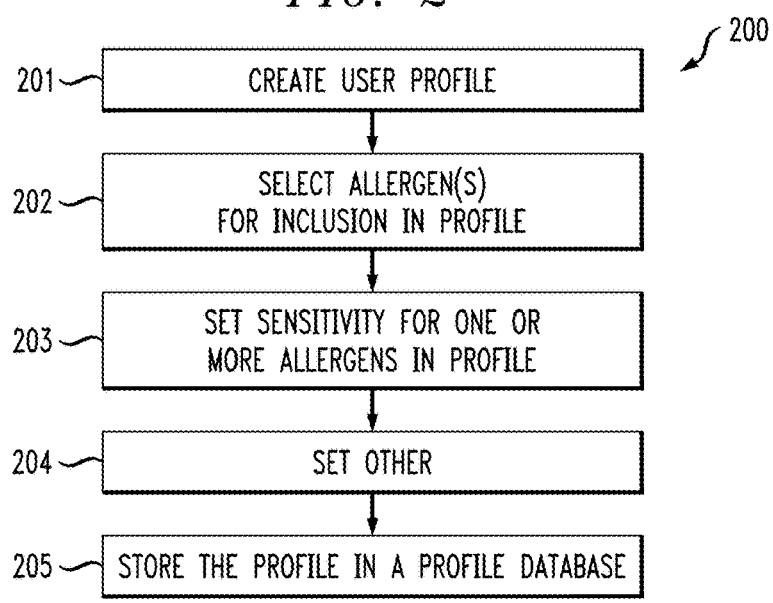
FIG. 2 is flow diagram of a method for creating a database of user profiles according to an embodiment of the present invention.
Figure 3A:
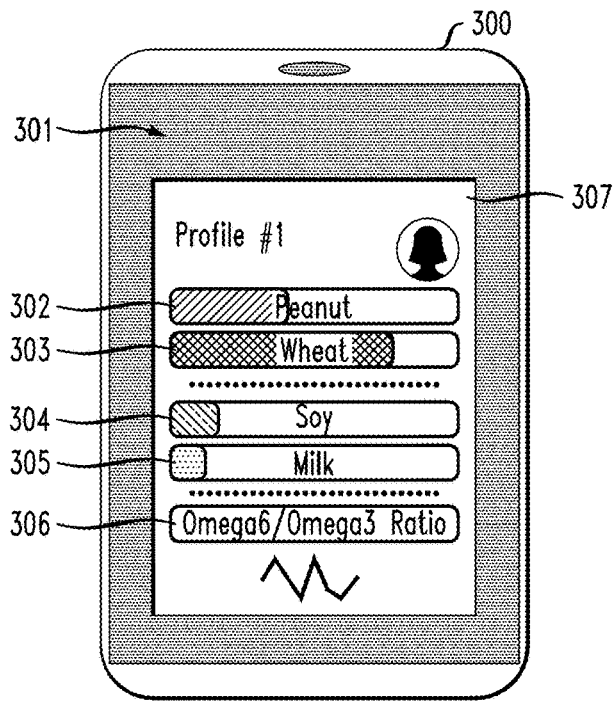
FIGS. 3A-B are illustrations of user profiles according to embodiment of the present invention.
Figure 3B:
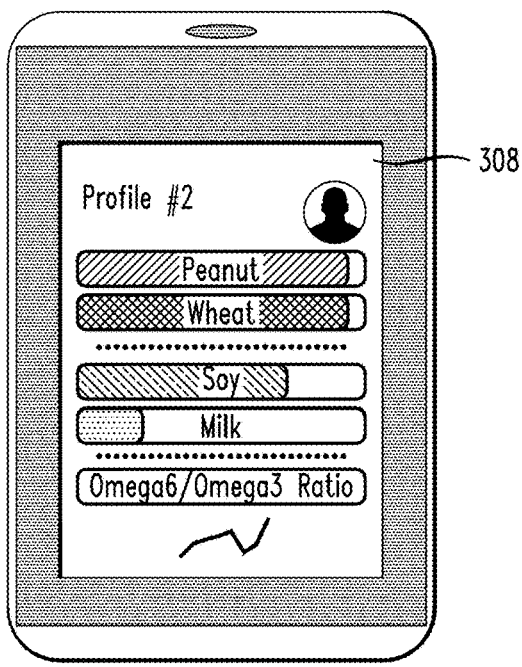

According to one or more embodiments of the present invention, the method includes gathering a user specific allergy profile and nutrition information 104. For example, the application supports the creation of an allergy profile (see FIG. 2 and FIGS. 3A-B). According to an embodiment of the present invention, in a method for generating a user profile 200, the user initializes a profile 201, selects allergens for inclusion in the profile 202 and sets sensitivities for one or more of the selected allergens. According to at least one embodiment of the present invention, a user can personalize allergens and sensitivity levels, for example, using a graphical user interface (GUI) 301 shown in FIG. 3A. In at least one exemplary embodiment, the user interacts with the graphical user interface (GUI) (e.g., through touch, text or speech based input) to select common allergens for inclusion in the allergy profile. The selected allergens are presented in the GUI that includes a slide bar or the like for setting a perceived sensitivity to the particular allergen. In one or more embodiments, the user enters known allergens and a perceived severity of each allergy. For example, the user sets a perceived sensitivity to peanuts 302 at about 40% and a perceived sensitivity to wheat products 303 at about 70%.

In at least one embodiment of the present invention, the application runs on a user device 300 to display a user interface 301 having user specified characteristics (see FIG. 3A), including for example, controls for specifying a severity of an allergy or reaction to tree nuts/peanuts 302, wheat 303, soybean 304, and milk products 305. The user interface 301 can further include user specified goals (see FIG. 2, block 204) for parameters such as a ratio of omega-6 to omega-3 essential fatty acids (EFA) 306.

The application enables the creation, selection and management of multiple user profiles, e.g., 307-308, which are stored in a database accessible to the application (e.g., on the user device 300, a cloud storage device, etc.) (see FIG. 2, block 205).

Figure 4:
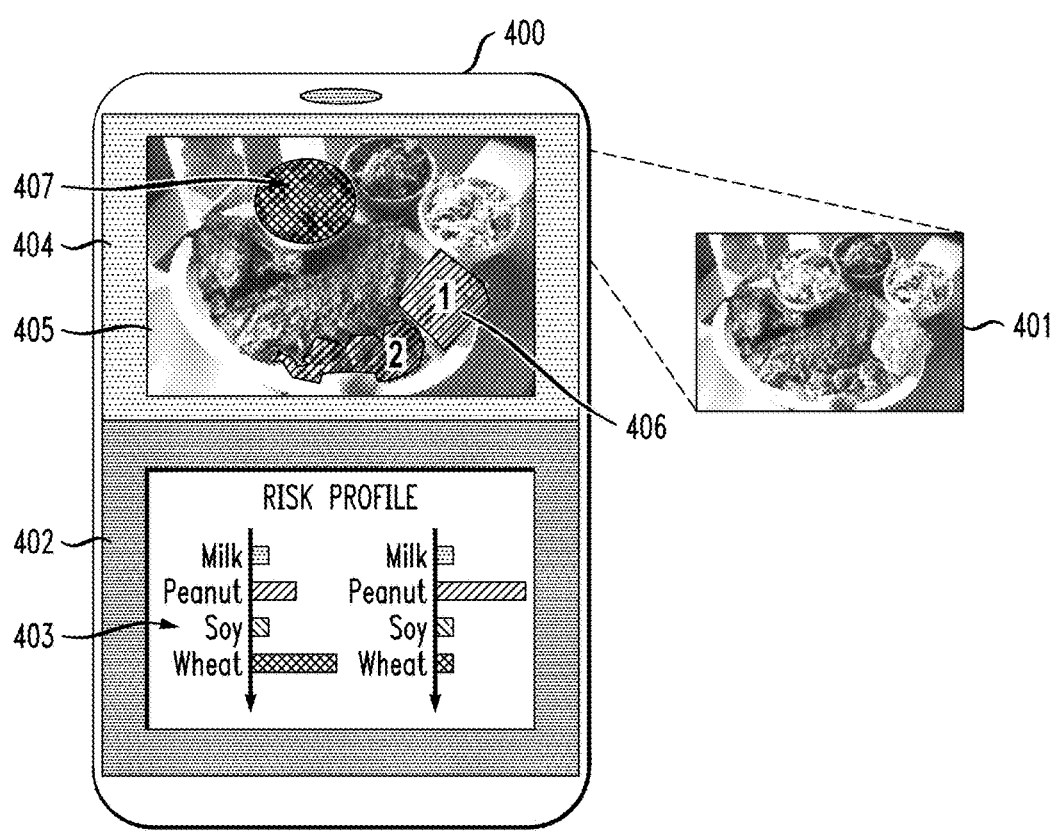
FIG. 4 is an illustration of a mobile device having a user interface according to an embodiment of the present invention.
Figure 5:
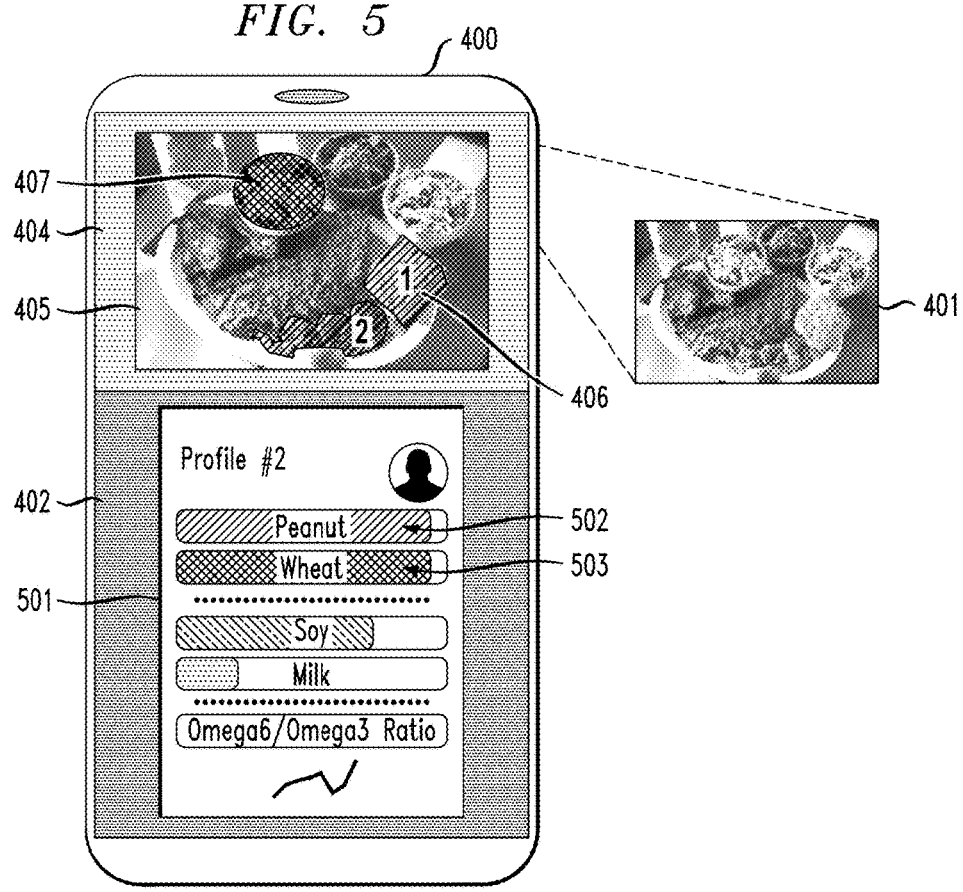
FIG. 5 is an illustration of a mobile device having a user interface according to an embodiment of the present invention.

According to one or more embodiments of the present invention, the method further includes identifying food substances with risk profiles matching a selected user allergy profile 105. For example, in FIGS. 4-5 a camera of the user device 400 captures an image of a scene including a plate of food 401. The application running on the user device 400 displays a unified GUI having a first portion 402 displaying a risk profile 403 determined for the food 401 and/or a selected user profile 501 and a second portion 404 displaying an output 405. The output 405 includes a view of the image that has been processed (e.g., segmented and classified). Segmented and classified objects are displayed in the output 405. The objects are identified, for example, by a color, intensity, pattern or the like. In FIGS. 4-5, a color coding is shown, where colors used to identify certain foods in the output 405 that match identifying colors used in the risk profile 403 and the selected user profile 501. For example, the output 405 distinguishes segmented foods classified and cross-referenced with the allergen database as likely to include peanuts using a red color 406, matching the red color used for a slide bar indicating the sensitivity to peanuts 502 in the profile 501. The foods classified and cross-references with the allergen database as likely to include wheat are identified by a green color 407 match the green color used for wheat 503 in the user profile 501.

Further shown in FIGS. 4-5 is a case where two food substances are identified as likely to include peanuts as an ingredient; these food substances are distinguished by the application in the output 405 by a numeral (i.e., "1" and "2"). It should be understood that different distinguishing characteristics can be used to link the output and the profile. Embodiments of the present invention are not limited to the examples provided herein.

According to one or more embodiments of the present invention, the user can use the output information (e.g., as shown in FIGS. 4-5) to guide further inquiry, tests, etc. For example, the user can confirm the automated detection using an additional sensor or additional image processing 106. According to an embodiment of the present invention, the additional sensor is a gluten sensor, which communicates (e.g., by a wireless interface) with the user device to provide additional data about the presence of wheat. Other sensors are contemplated, such as a handheld spectrometer or an integrated (in the user device) photonic chip sensor. According to at least one embodiment of the present invention, the additional data 106 is used to update the risk profile 103.

According to one or more embodiments of the present invention, a combination of computer vision and physical sensor devices are used to detect food substances.

According to at least one embodiment of the present invention, the application can receive input from one or more physical sensors configured to detect compounds from volatile particles in the surrounding air (e.g., electronic noses for detecting odors), which sample food and detect food substances, which can be hidden below surface layers. According to one or more embodiments of the present invention, the application identifies risky portions of food using the image segmentation and classification, and suggests (via a unified GUI showing the segmented and classified image and risk profile and/or user profile) sections of the food to be tested by a physical sensor. Such a suggestion can be an indication (e.g., color or text identifying the risky portion) in the GUI of the user's device. In such a manner, detection sensitivity can be improved via guided testing of food.

According to one or more embodiments of the present invention, volatile gases can be detected by the user's device having an integrated photonic chip sensor, which can detect gases using a miniaturized silicon photonics spectroscopic device can correlate the detected gases to the food content. According to one or more embodiments of the present invention, linoleic acid (typical of omega-6) and alpha-linolenic acid (typical of omega-3) are detected, and a ratio of these fatty acids in the food is determined. For this analysis, a food sample fed through a miniaturized HPLC (High Performance Liquid Chromatography) unit with UV (ultraviolet) detector can be used.

According to one or more embodiments of the present invention, physical sensors, including volatile organic compound (VOC) sensors, electrochemical, or multispectral, to provide high specificity of detection. One or more sensors may require proximity to food, and/or physical contact with food. According to one or more embodiments of the present invention, the sensors sample a generalized area of food (e.g., without physical contact) or a localized specific regions (e.g., through physical contact).

According to one or more embodiments of the present invention, a physical sensor of the user's device detects and measures the presence of sugars, tree nuts, peanuts, gluten, or other allergens.

According to one or more embodiments of the present invention, a physical sensor of the user's device detects and measures the presence of contaminants, such as pesticides and preservatives.

Recapitulation:

According to at least one embodiment of the present invention, a method of displaying information relating to an allergen present in a food substance together with a user profile, the method including capturing an image of a scene, segmenting the image to determining at least a segmentation of the food substance in the image, determining a classification of the food substance using the segmentation, determining a presence of the allergen in the food substance using the classification of the food substance and a database of allergens and food substances, determining a risk to a user using the user profile specifying a user sensitivity to the allergen, and displaying an output including a view of the user profile and the image, wherein the image is augmented to identify the presence of the allergen.

The methodologies of embodiments of the disclosure may be particularly well-suited for use in an electronic device or alternative system. Accordingly, embodiments of the present invention may take the form of an entirely hardware embodiment or an embodiment combining software and hardware aspects that may all generally be referred to herein as a "processor," "circuit," "module" or "system."

Furthermore, it should be noted that any of the methods described herein can include an additional step of providing a computer system for displaying information relating to an allergen present in a food substance together with a user profile. Further, a computer program product can include a tangible computer-readable recordable storage medium with code adapted to be executed to carry out one or more method steps described herein, including the provision of the system with the distinct software modules.

Figure 6:
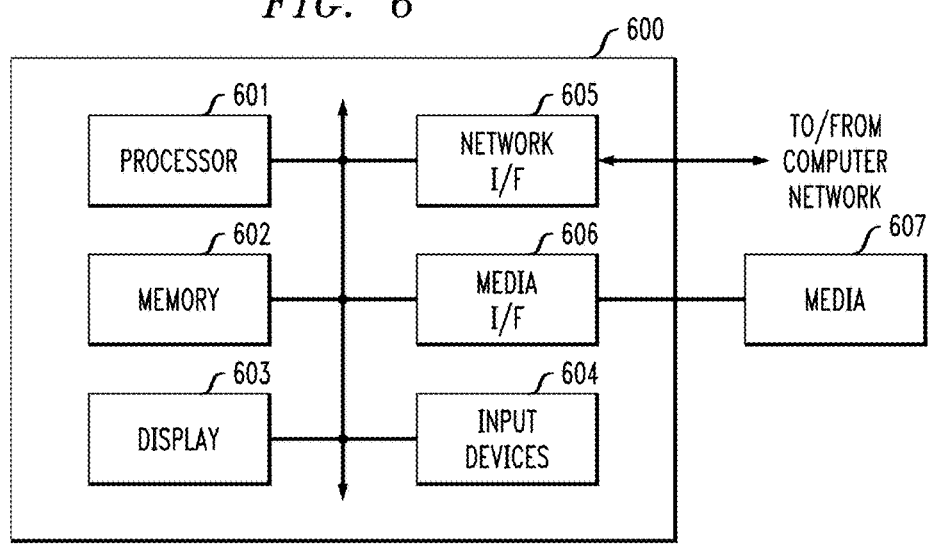
FIG. 6 is a block diagram depicting an exemplary computer system for controlling an interface according to an exemplary embodiment of the present invention.

Referring to FIG. 6; FIG. 6 is a block diagram depicting an exemplary computer system configured to identify a specific food substance according to an embodiment of the present invention. The computer system shown in FIG. 6 includes a processor 601, memory 602, display 603, input device 604 (e.g., keyboard), a network interface (I/F) 605, a media I/F 606, and media 607, such as a signal source, e.g., camera, Hard Drive (HD), external memory device, etc.

In different applications, some of the components shown in FIG. 6 can be omitted. The whole system shown in FIG. 6 is controlled by computer readable instructions, which are generally stored in the media 607. The software can be downloaded from a network (not shown in the figures), stored in the media 607. Alternatively, software downloaded from a network can be loaded into the memory 602 and executed by the processor 601 so as to complete the function determined by the software.

The processor 601 may be configured to perform one or more methodologies described in the present disclosure, illustrative embodiments of which are shown in the above figures and described herein. Embodiments of the present invention can be implemented as a routine that is stored in memory 602 and executed by the processor 601 to process the signal from the media 607. As such, the computer system is a general-purpose computer system that becomes a specific purpose computer system when executing routines of the present disclosure.

Although the computer system described in FIG. 6 can support methods according to the present disclosure, this system is only one example of a computer system. Those skilled of the art should understand that other computer system designs can be used to implement embodiments of the present invention.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A method of displaying information relating to an allergen present in a food substance together with a user profile, the method comprising:
    capturing an image of a scene;
    segmenting the image to determining at least a segmentation of the food substance in the image;
    determining a classification of the food substance using the segmentation;
    determining a presence of the allergen in the food substance using the classification of the food substance and a database of allergens and food substances;
    determining a risk to a user using the user profile specifying a user sensitivity to the allergen; and
    displaying an output including a view of the user profile and the image, wherein the image is augmented to identify the presence of the allergen, wherein the augmentation comprises displaying, in an augmented view of the image, an identifying characteristic identifying the presence of the allergen that is common to the user profile.

2. The method of claim 1, wherein the identifying characteristic is one of color, intensity and pattern.

3. The method of claim 1, further comprising applying a further identifying characteristic to differentiate between two food substances determined to include the allergen.

4. The method of claim 1, further comprising receiving a user selection of the user profile from among a plurality of user profiles stored in a user profile database.

5. The method of claim 1, further comprising determining a ratio of omega-3 to omega-6 for the food substance using the classification of the food substance and a database of ratios of omega-3 to omega-6 for a plurality of food substances.

6. The method of claim 1, wherein the display of the identifying characteristic in the augmented view of the image is matched by a display of the identifying characteristic in the view of the user profile for the allergen.

7. A non-transitory computer readable medium comprising computer executable instructions which when executed by a computer cause the computer to perform a method of displaying information relating to an allergen present in a food substance together with a user profile, the method comprising:
   capturing an image of a scene;
   segmenting the image to determining at least a segmentation of the food substance in the image;
   determining a classification of the food substance using the segmentation;
   determining a presence of the allergen in the food substance using the classification of the food substance and a database of allergens and food substances;
   determining a risk to a user using the user profile specifying a user sensitivity to the allergen; and
   displaying an output including a view of the user profile and the image, wherein the image is augmented to identify the presence of the allergen, wherein the augmentation comprises displaying, in an augmented view of the image, an identifying characteristic identifying the presence of the allergen that is common to the user profile.

8. The computer readable medium of claim 7, wherein the identifying characteristic is one of color, intensity and pattern.

9. The computer readable medium of claim 7, further comprising applying a further identifying characteristic to differentiate between two food substances determined to include the allergen.

10. The computer readable medium of claim 7, further comprising receiving a user selection of the user profile from among a plurality of user profiles stored in a user profile database.

11. The computer readable medium of claim 7, further comprising determining a ratio of omega-3 to omega-6 for the food substance using the classification of the food substance and a database of ratios of omega-3 to omega-6 for a plurality of food substances.

12. The computer readable medium of claim 7, wherein the display of the identifying characteristic in the augmented view of the image is matched by a display of the identifying characteristic in the view of the user profile for the allergen.

13. A method of displaying information relating to an allergen present in a food substance together with a user profile, the method comprising:
   capturing, by a camera of a mobile device, an image of a scene;
   segmenting, by a processor of the mobile device, the image to determining at least a segmentation of the food substance in the image;
   determining, by the processor of the mobile device, a classification of the food substance using the segmentation;
   determining, by the processor of the mobile device, a presence of the allergen in the food substance using the classification of the food substance and a database of allergens and food substances;
   determining, by the processor of the mobile device, a risk to a user using the user profile specifying a user sensitivity to the allergen; and
   displaying, by a display of the mobile device, an output including a view of the user profile and the image, wherein the image is augmented to identify the presence of the allergen wherein the augmentation comprises displaying, by the display of the mobile device in an augmented view of the image, an identifying characteristic identifying the presence of the allergen that is common to the user profile.

14. The method of claim 13, wherein the identifying characteristic is one of color, intensity and pattern.

15. The method of claim 13, further comprising applying, by the processor of the mobile device, a further identifying characteristic, displayed by the display of the mobile device, to differentiate between two food substances determined to include the allergen.

16. The method of claim 13, further comprising receiving, by the mobile device, a user selection of the user profile from among a plurality of user profiles stored in a user profile database.

17. The method of claim 13, further comprising determining, by the processor of the mobile device, a ratio of omega-3 to omega-6 for the food substance using the classification of the food substance and a database of ratios of omega-3 to omega-6 for a plurality of food substances.

18. The method of claim 13, wherein the database of allergens and food substances is stored on one of a memory of the mobile device accessible to the processor and a remote server accessible to the processor.

19. The method of claim 13, further comprising:
   receiving sensor data from a remote sensor; and
   updating the determination of the risk to the user using the sensor data.

20. The method of claim 13, wherein the display of the identifying characteristic in the augmented view of the image is matched by a display of the identifying characteristic in the view of the user profile for the allergen.

* * * * *